US006982352B2

(12) United States Patent
Lappe et al.

(10) Patent No.: US 6,982,352 B2
(45) Date of Patent: Jan. 3, 2006

(54) PROCESS FOR PREPARING N-METHYLDIALKYLAMINES FROM SECONDARY DIALKYLAMINES AND FORMALDEHYDE

(75) Inventors: Peter Lappe, Dinslaken (DE); Helmut Springer, Dinslaken (DE)

(73) Assignee: Celanese Chemicals Europe GmbH, (DE)

( * ) Notice: Subject to any disclaimer, the term of this patent is extended or adjusted under 35 U.S.C. 154(b) by 32 days.

(21) Appl. No.: 10/804,747

(22) Filed: Mar. 19, 2004

(65) Prior Publication Data

US 2004/0204611 A1    Oct. 14, 2004

(30) Foreign Application Priority Data

Apr. 10, 2003   (DE) ................ 103 16 375

(51) Int. Cl.
C07C 209/28 (2006.01)
C07C 211/35 (2006.01)
C07C 211/08 (2006.01)
C07C 211/21 (2006.01)
C07C 211/27 (2006.01)

(52) U.S. Cl. ................ 564/471; 564/472; 564/473
(58) Field of Classification Search ................ 564/471, 564/472, 473
See application file for complete search history.

(56) References Cited

U.S. PATENT DOCUMENTS

| 2,298,284 | A | * | 10/1942 | Emerson ................ 564/397 |
|---|---|---|---|---|
| 3,025,313 | A | * | 3/1962 | Gunderson ................ 554/58 |
| 3,136,765 | A | * | 6/1964 | Dimroth et al. ............ 544/170 |
| 3,136,819 | A | * | 6/1964 | Pilch et al. ................ 564/473 |
| 3,210,349 | A | * | 10/1965 | Godfrey .................... 544/162 |
| 4,190,601 | A | * | 2/1980 | Decker et al. ............. 564/374 |
| 4,757,144 | A | * | 7/1988 | Okabe et al. .............. 544/404 |
| 4,952,734 | A | * | 8/1990 | Weber et al. .............. 564/471 |
| 5,091,584 | A | * | 2/1992 | Brake ......................... 564/471 |
| 5,091,585 | A | * | 2/1992 | Su et al. .................... 564/473 |
| 5,457,233 | A | * | 10/1995 | Ouziel ....................... 564/473 |
| 5,773,658 | A | * | 6/1998 | Weber et al. .............. 564/473 |
| 6,252,071 | B1 | * | 6/2001 | Muller et al. .............. 544/111 |
| 2002/0169313 | A1 | * | 11/2002 | Gao et al. .................. 540/484 |

FOREIGN PATENT DOCUMENTS

DE    80 520    3/1895
DE    287802    10/1915

OTHER PUBLICATIONS

Blicke et al., Journal of the American Chemical Society (1939), vol. 61, pp. 93-95.*
Eschweiler, Berichte (1905), vol. 38 pp. 880-882.*
Plochl, Berichte (1888), vol. 21, pp. 2117-2119.*

* cited by examiner

*Primary Examiner*—Brian Davis
(74) *Attorney, Agent, or Firm*—Charles A. Muserlian

(57) ABSTRACT

The present invention relates to a process for preparing N-methyldialkyl-amines by reacting secondary dialkylamines with formaldehyde at a temperature of from 100 to 200° C., by using from 1.5 to 3 mol of formaldehyde per mole of secondary dialkylamine and degassing the resulting reaction product, removing the aqueous phase and distilling the organic phase.

7 Claims, No Drawings

PROCESS FOR PREPARING N-METHYLDIALKYLAMINES FROM SECONDARY DIALKYLAMINES AND FORMALDEHYDE

STATE OF THE ART

The present invention relates to a process for preparing N-methyldialkylamines from secondary amines and formaldehyde.

Tertiary amines and especially N-methyldialkylamines, as important intermediates for the chemical industry, have great economic significance. They are used as vulcanization accelerants in the rubber industry or as polymerization and curing catalysts for the production of plastics moldings based on epoxide and polyurethane. They are also suitable as corrosion inhibitors and as starting materials for detergents and flocculants. N-Methyldialkylamines have likewise gained significance as important intermediates for the preparation of pharmaceutical products or of substances which are used in the crop protection field.

As a consequence of the high industrial significance of N-methyldialkylamines, there are numerous indications in the economic and technical literature for their preparation.

The preparation of tertiary amines starting from secondary amines by reacting with carbonyl compounds in the presence of formic acid according to Leuckart-Wallach is known (Houben-Weyl; page 648; Methodicum Chimicum p. 541). Formic acid serves as reducing agent and is usually used in the form of formamide or ammonium formate.

When the starting carbonyl component is formaldehyde, the reaction with secondary amines carried out in the presence of formic acid leads to N-methyldialkylamines. In this method, named after Eschweiler-Clarke, 1–1.25 mol of formaldehyde and 2–4 mol of formic acid are commonly used per mole of amine (Methodicum Chimicum, Volume 6, p. 543, Georg Thieme Verlag, Stuttgart 1974). A more recent development in this method is the N-methylation of amines under microwave irradiation (Synthetic Communications (1996), 26 (21), 3919–3922).

Aliphatic secondary amines may also be methylated to tertiary amines by heating with formaldehyde to 120–160° C. According to Hoppe Seyler's Zeitschrift fur Physiologische Chemie, Walter de Gruyter & Co., 196, 1931, pages 81–86, the methylation reaction can be carried out in the presence of 10% formaldehyde solution with the addition of calcium chloride or with the use of paraformaldehyde. In the existing method, the aliphatic secondary amine is used in the form of its hydrochloride. A large addition of formaldehyde is also required, and up to 42 mol of paraformaldehyde are used per mole of aliphatic secondary amine.

Berichte 45, 1912, pages 2404–2409 also reports the action of a 40% solution of formaldehyde of phenylethylamine chlorohydrate to give N-dimethylphenylethylamine.

The literature additionally describes numerous further methods for preparing N-methyldialkylamines. For example, N-methyldi-n-propylamine may be obtained in good yields by reacting di-n-propylamine with methyl iodide (Chem. Ber. 33, 1900, 1439–1440). Instead of methyl iodide, it is also possible to use dimethyl sulfate as the alkylating agent (J. Chem. Soc. 105, 1914, 2766) or methyltrimethoxyphosphonium tetrafluoroborate (J. Org. Chem. 49 (25), 1984, 4877–4880).

On the industrial scale, N-methyldialkylamines are prepared from formaldehyde and secondary amines by catalytically hydrogenating with hydrogen over metal catalyst, for example over nickel or palladium catalysts.

According to U.S. Pat. No. 4,757,144, tertiary amines are prepared from primary or secondary amines and formaldehyde by a suspension hydrogenation in the presence of palladium or platinum catalysts. The hydrogenation is carried out at a temperature of from 80° C. to 180° C. and a pressure of from 0.29 to 4.9 MPa gauge.

EP-A1-0 492 771 likewise describes a catalytic process for preparing N-methyldialkylamines starting from secondary alkylamines in the presence of formaldehyde. The reactants are reacted over fixed bed catalyst at a pressure of from 0.8 to 28 MPa and a temperature of from 100 to 150° C.

The catalyst used is a nickel catalyst doped with transition metals, preferably with copper and chromium.

DE-A1-35 44 510 is also concerned with the preparation of aliphatic tertiary amines starting from primary or secondary amines by reacting with formaldehyde. The N-methylolamines which are initially formed are subsequently hydrogenated in suspension over finely divided palladium or palladium catalysts at temperatures of from 50 to 200° C. and pressures of from 0.1 to 10 MPa.

The existing processes for preparing N-methyldialkylamines starting from secondary alkylamines and formaldehyde either require the presence of a specific added reducing agent, for example formic acid, or of a hydrogenation catalyst and hydrogen. Both process variants are costly and inconvenient, since the use of specific reducing agents such as formic acid requires specially designed apparatus materials as a consequence of its corrosive action. It is also costly and inconvenient to provide a catalytic hydrogenation stage carried out with hydrogen, which additionally requires a hydrogen source and also supply with metallic hydrogenation catalysts. The disposal of the exhausted hydrogenation catalysts likewise has to be taken into account. There is therefore a need for a very simple and inexpensive process for preparing N-methyldialkylamines.

SUMMARY OF THE INVENTION

It has been found that, surprisingly, secondary alkylamines can be converted in very high yields to the corresponding N-methyldialkylamines with only a small excess of formaldehyde.

The invention therefore consists in a process for preparing N-methyldialkylamines from secondary dialkylamines and formaldehyde at a temperature of from 100 to 200° C. The process comprises using from 1.5 to 3 mol of formaldehyde per mole of secondary dialkylamine, degassing the resulting reaction product, removing the aqueous phase and distilling the organic phase.

Surprisingly, at the selected molar ratio of dialkylamine to formaldehyde, the desired N-methyldialkylamines can be obtained in high yields in a simple manner. Without wishing to mechanistically interpret the progress of the reaction, it is assumed that the reaction proceeds from 1 mol of secondary alkylamine with 1.5 mol of formaldehyde by the following stoichiometry:

$$2R_2NH + 3HCHO \rightarrow 2R_2N\text{---}CH_3 + CO_2 + H_2O$$

It is therefore essential for the performance of the claimed process to limit the amount of formaldehyde which is above the stoichiometrically required amount to a narrow range, in order to suppress the formation of undesired by-products and to keep the loss of starting materials low. From 1.5 to 3, preferably from 1.5 to 2.5, mol of formaldehyde have to be used per mole of secondary alkylamine.

The claimed process is carried out at a temperature of from 100 to 200° C., preferably from 120 to 160° C.

Operation is effected at autogenous pressure which is attained as a consequence of the selected reaction temperature. The reaction may be conducted continuously or batchwise.

On completion of the reaction, the reaction product comprising water and the organic phase is initially removed and then degassed, in order to drive out $CO_2$ formed. To this end, the crude mixture is cooled and, optionally after addition of an organic solvent such as isopropanol, is treated at elevated temperature under atmospheric pressure, in some cases even distilled. The temperature range to be selected depends upon the boiling range of the organic products, in particular upon the boiling points of the dialkylamine and of the desired N-methyldialkylamines, and is generally within a temperature range from 50 to 150° C.

After the degassing of the reaction mixture, the organic product phase is separated from the aqueous phase, for example by passing through a membrane or by simple phase separation, optionally after addition of an organic solvent such as n-hexene-1 to promote the phase separation. This is followed by the fractional distillation of the crude product freed of water under conventional conditions.

Formaldehyde is typically used as an aqueous solution having a concentration of from 10 to 60% by weight. Preference is given to using an aqueous formaldehyde solution having a formaldehyde content of from 25 to 40% by weight.

The secondary dialkylamine is added in undiluted form without the addition of solvent. Useful secondary dialkylamines are mixed or symmetrical cycloaliphatic or aliphatic dialkylamines having straight-chain or branched, saturated or unsaturated alkyl groups each having from 2 to 20 carbon atoms, in particular from 2 to 15, preferably from 2 to 9 carbon atoms, or having arylalkyl groups each having from 7 to 15 carbon atoms.

Representative of cycloaliphatic secondary amines are dicyclohexylamine, and, of aliphatic secondary amines, di-n-propylamine, di-n-butylamine, di-n-pentylamine, di-2-ethylhexylamine and diisononylamine.

However, mixed cycloaliphatic, aliphatic dialkylamines such as N-ethylcyclohexylamine can also be converted to tertiary amines by the process according to the invention. A representative of secondary dialkylamines having unsaturated alkyl groups is diallylamine. Dibenzylamine is an example of a secondary dialkylamine having arylalkyl groups.

The process according to the invention is particularly suitable for preparing N-methyldi-n-butylamine and N-methyldi-n-propylamine.

The claimed method permits elegant and simple access to N-methyldialkylamines in surprisingly high yields, and the by-products obtained are only water and carbon dioxide which can be removed from the reaction mixture without any problem. In contrast, the existing processes are without exception more complex and afford the desired N-methyl-dialkylamines in usually lower yields.

The examples cited hereinbelow demonstrate the invention without limiting it.

EXAMPLE 1

Preparation of N-methyldiethylamine 149.3 g (2.0 mol) of diethylamine (98%) and 330.2 g (3.2 mol) of formaldehyde (29.1%) are initially charged in a 1 l autoclave and heated to 120° C. The reaction time at this temperature is 8 hours, and a maximum pressure of 1.44 MPa is established. Afterwards, the reaction mixture is cooled and worked up by distillation.

To this end, the crude amine (aqueous and organic phase) is admixed with 200.0 g of isopropanol, transferred to a 1 l flask and slowly heated with stirring to 60° C. Gentle evolution of gas begins and is complete when a temperature of approx. 75° C. has been attained. Afterwards, distillation from the residue is effected at atmospheric pressure; an amount of 614.4 g of distillate is isolated. This distillate is passed through a membrane to remove water and subsequently fractionally distilled; the amine boils at 63–65° C. 168.8 g of product of value having a purity of 96.0% are isolated, corresponding to a yield of 93.0% of theory.

EXAMPLE 2

Preparation of N-methyldi-n-butylamine

In a similar manner to Example 1, 258.5 g (2.0 mol) of di-n-butylamine and 330.2 g (3.2 mol) of formaldehyde (29.1%) are reacted in a 1 l autoclave; a maximum pressure of 3.2 MPa is established at a temperature of 120° C. After the crude amine (aqueous and organic phase) has been degassed at a maximum temperature of 80° C., the water is removed on a water separator. The remaining organic phase is subsequently fractionally distilled. 274.6 g of N-methyldi-n-butylamine having a purity of 99.6% are isolated, corresponding to a yield of 95.6% of theory.

EXAMPLE 3

Preparation of N-methyl-N-ethyl-n-butylamine

In a similar manner to Example 1, 202.4 g (2.0 mol) of N-ethyl-n-butylamine and 330.2 g (3.2 mol) of formaldehyde (29.1%) are reacted in a 1 l autoclave; a maximum pressure of 2.2 MPa is established at a temperature of 120° C. After the crude amine (aqueous and organic phase) has been degassed at a maximum temperature of 88° C., the water is removed on a water separator. The remaining organic phase is subsequently fractionally distilled. 223.0 g of N-methyl-N-ethyl-n-butylamine having a purity of 97.8% are isolated, corresponding to a yield of 94.7% of theory.

EXAMPLE 4

Preparation of N-methyl-N-ethyl-1,2-dimethylpropylamine

In a similar manner to Example 1, 230.4 g (2.0 mol) of N-ethyl-1,2-dimethylpropylamine and 330.2 g (3.2 mol) of formaldehyde (29.1%) are reacted in a 1 l autoclave; a maximum pressure of 2.3 MPa is established at a temperature of 120° C. After the crude amine (aqueous and organic phase) has been degassed at a maximum temperature of 94° C., the water is removed on a water separator. The remaining organic phase is subsequently fractionally distilled. 251.7 g of N-methyl-N-ethyl-1,2-dimethylpropylamine having a purity of 98.6% are isolated, corresponding to a yield of 96.0% of theory.

EXAMPLE 5

Preparation of N-methyldiamylamine

In a similar manner to Example 1, 314.4 g (2.0 mol) of diamylamine (technical mixture of 18.3% by weight of diisopentylamine, 61.0% by weight of di-n/i-pentylamine and 19.2% by weight of di-n-pentylamine, remainder: 1.5% by weight) and 330.2 g (3.2 mol) of formaldehyde (29.1%)

are reacted in a 1 l autoclave; a maximum pressure of 2.5 MPa is established at a temperature of 120° C. After the crude amine (aqueous and organic phase) has been degassed at a maximum temperature of 102° C., the water is removed on a water separator. The remaining organic phase is subsequently distilled. 329.1 g of N-methyldiamylamine having a purity of 91.8% are isolated, corresponding to a yield of 88.3% of theory.

EXAMPLE 6

Preparation of N-methyldi-2-ethylhexylamine

In a similar manner to Example 1, 181.1 g (0.75 mol) of di-2-ethylhexylamine and 193.5 g (1.88 mol) of formaldehyde (29.1%) are reacted in a 1 l autoclave; a maximum pressure of 1.9 MPa is established at a temperature of 160° C. After the crude amine (aqueous and organic phase) has been degassed at a maximum temperature of 100° C., the water is removed with the addition of 50 g of n-hexene-1 on a water separator. The remaining organic phase is subsequently distilled. 185.1 g of N-methyldi-2-ethylhexylamine having a purity of 91.4% are isolated, corresponding to a yield of 88.3% of theory.

EXAMPLE 7

Preparation of N-methyldiisononylamine

In a similar manner to Example 1, 202.1 g (0.75 mol) of diisononylamine and 170.3 g (1.65 mol) of formaldehyde (29.1%) are reacted in a 1 l autoclave; a maximum pressure of 1.9 MPa is established at a temperature of 160° C. After the end of the reaction, the organic phase is removed from the aqueous phase; the remaining organic phase is subsequently distilled. 208.0 g of N-methyldiisononylamine having a purity of 85.0% are isolated, corresponding to a yield of 83.2% of theory.

EXAMPLE 8

Preparation of N-methyl-N-ethylcyclohexylamine

In a similar manner to Example 1, 190.8 g (1.5 mol) of N-ethylcyclohexylamine and 247.6 g (2.4 mol) of formaldehyde (29.1%) are reacted in a 1 l autoclave; a maximum pressure of 2.6 MPa is established at a temperature of 160° C. After the end of the reaction, 30 g of hexene-1 are added and the organic phase is removed from the aqueous phase. The remaining organic phase is subsequently fractionally distilled. 196.9 g of N-methyl-N-ethylcyclohexylamine having a purity of 98.7% are isolated, corresponding to a yield of 91.8% of theory.

EXAMPLE 9

Preparation of N-methyldibenzylamine

In a similar manner to Example 1, 197.3 g (1.0 mol) of dibenzylamine and 165.1 g (1.6 mol) of formaldehyde (29.1%) are reacted in a 1 l autoclave; a maximum pressure of 1.8 MPa is established at a temperature of 160° C. After the end of the reaction, 30 g of hexene-1 are added and the organic phase is removed from the aqueous phase. The remaining organic phase is subsequently distilled. 191.8 g of N-methyldibenzylamine having a purity of 93.8% are isolated, corresponding to a yield of 85.1% of theory.

EXAMPLE 10

Preparation of N-methyldicyclohexylamine

In a similar manner to Example 1, 204.0 g (1.13 mol) of dicyclohexylamine and 185.5 g (1.80 mol) of formaldehyde (29.1%) are reacted in a 1 l autoclave; a maximum pressure of 2.4 MPa is established at a temperature of 160° C. After the end of the reaction, 50 g of hexene-1 are added and the organic phase is removed from the aqueous phase. The remaining organic phase is subsequently distilled. 226.3 g of N-methyldicyclohexylamine having a purity of 93.7% are isolated, corresponding to a yield of 96.1% of theory.

EXAMPLE 11

Preparation of N-methyldiallylamine

In a similar manner to Example 1, 194.3 g (2.0 mol) of diallylamine and 330.2 g (3.2 mol) of formaldehyde (29.1%) are reacted in a 1 l autoclave; a maximum pressure of 2.5 MPa is established at a temperature of 120° C. After the crude amine (aqueous and organic phase) has been degassed at a maximum temperature of 87° C., the water is removed on a water separator. The remaining organic phase is subsequently fractionally distilled. 216.3 g of N-methyldiallylamine having a purity of 95.7% are isolated, corresponding to a yield of 93.1% of theory.

What is claimed is:

1. A process for preparing N-methyldialkylamines from secondary dialkylamines or diaryalkylamines and formaldehyde at a temperature of from 100 to 200° C., which comprises using from 1.5 to 3 mol of formaldehyde per mole of secondary dialkylamine, or diaryalkylamines, degassing the resulting reaction product, removing the aqueous phase and distilling the organic phase.

2. The process as claimed in claim 1, wherein from 1.5 to 2.5 mol of formaldehyde are used per mole of secondary dialkylamine.

3. The process as claimed in claim 1, wherein the reaction is effected at a temperature from 120 to 160° C.

4. The process as claimed in claim 1, wherein the secondary dialkylamines or diaryalkylamines used are mixed or symmetrical cycloaliphatic or aliphatic dialkylamines having straight-chain or branched, saturated or unsaturated alkyls of 2 to 20 carbon atoms or having arylalkyls of 7 to 15 carbon atoms.

5. The process as claimed in claim 4, wherein the secondary dialkylamines or diaryalkylamines used are mixed or symmetrical cycloaliphatic or aliphatic dialkylamines having straight-chain or branched, saturated or unsaturated alkyls of 2 to 15 carbon atoms.

6. The process as claimed in claim 1 wherein the dialkylamine is di-n-butylamine or di-n-propylamine.

7. The process of claim 5 wherein the alkyls have 2 to 9 atoms.

* * * * *